United States Patent [19]

Chung

[11] Patent Number: 5,379,028

[45] Date of Patent: Jan. 3, 1995

[54] HEIGHT MEASUREMENT DEVICE WITH VOICE READOUT

[75] Inventor: Caleb Chung, Van Nuys, Calif.

[73] Assignee: With Design In Mind, Chatsworth, Calif.

[21] Appl. No.: 29,626

[22] Filed: Mar. 11, 1993

[51] Int. Cl.⁶ .......................... G08B 25/08; A61B 1/00
[52] U.S. Cl. ...................................... 340/692; 33/512; 340/384.1; 446/397
[58] Field of Search ............... 340/692, 573, 555, 686, 340/384 E, 384.3, 384.1; 33/512; 177/45, 245; 446/175, 397; 128/905

[56] References Cited

U.S. PATENT DOCUMENTS

| | | | |
|---|---|---|---|
| 2,215,884 | 9/1940 | Runge | 33/512 |
| 3,616,690 | 11/1971 | Harden | 177/245 X |
| 3,808,694 | 5/1974 | Hutchinson et al. | 177/245 X |
| 4,008,524 | 2/1977 | Allen | 33/512 |
| 4,366,873 | 1/1983 | Levy et al. | 340/692 X |
| 4,518,052 | 5/1985 | Chen | 177/245 |
| 4,603,828 | 8/1986 | Farley, Jr. et al. | 33/512 X |
| 4,923,024 | 5/1990 | Ferrer et al. | 177/245 |
| 5,193,541 | 3/1993 | Hatsuwi | 28/906 X |

Primary Examiner—John K. Peng
Assistant Examiner—Thomas J. Mullen, Jr.
Attorney, Agent, or Firm—Kelly Bauersfeld & Lowry

[57] ABSTRACT

A mechanical slide carrying a measuring arm is movable in relation to a vertical scale, in association with voice commands and/or other novelty audio signals to position the measuring arm on top of a person's head, at a position representing the person's height. Depression of a readout button then activates a voice readout of the measured height.

16 Claims, 4 Drawing Sheets

HEIGHT MEASUREMENT DEVICE WITH VOICE READOUT

BACKGROUND OF THE INVENTION

This invention relates generally to measurement devices for quickly and easily measuring a person's height. More particularly, this invention relates to a novelty height measurement device which is operated in conjunction with a sequence of voice commands and/or other audio signals, and provides a synthesized voice readout of the measured height of a person.

Children and adolescents commonly have a strong interest in frequent height measurements for purposes of monitoring their individual growth. In this regard, such height measurements are normally performed by having the person stand against a wall in a position alongside a measuring stick or tape, while a second person reads the measured height. In some instances, a permanent measuring scale or other measurement markings are applied to the wall to facilitate frequent height measurements. However, the assistance of a second person, typically a parent or other adult, has normally been required.

The present invention relates a height measurement device adapted for mounting onto a wall, wherein the device can be manipulated quickly and easily by a child for purposes of obtaining a height measurement without requiring the assistance of another person.

SUMMARY OF THE INVENTION

In accordance with the invention, a height measurement device is provided for use by a single person, such as a child, to obtain an accurate height measurement in a quick and easy manner. The measurement device includes voice synthesizer means and/or additional audio signals to produce a novelty measurement device which provides, in the preferred form, a voice readout of measured height.

The height measurement device comprises a relatively lightweight housing adapted for mounting onto a wall, such as a bedroom wall in a residential dwelling. The housing includes a vertical scale in association with a vertical slide track which carries a mechanical slide for vertical displacement along the track in relation to the scale. The mechanical slide in turn carries a measurement arm adapted for movement to a deployed, generally horizontal position.

An electronic control circuit is mounted within the device housing and includes voice and/or audio synthesizer means for operation in conjunction with vertical displacement of the slide. When the slide with measurement arm thereon in moved to a vertical position representing the measured height of a person, the voice readout means is activated for providing a synthesized voice readout of the measured height.

In the current preferred form of the invention, vertical displacement of the slide rotatably drives an apertured sensor wheel mounted in association with an optical sensor unit. The control circuit is connected to the optical sensor unit and responds to the direction of sensor wheel rotation to incrementally follow the vertical position of the slide. Novelty voice and/or audio signals are generated as the slide is moved up and down along the slide track. In addition, depression of a start button activates the electronic control circuit for providing a sequence of interactive commands and greetings and/or other audio signals to facilitate manipulation of the device by a small child. When the measurement arm is positioned on top of the person's head, in a position representing the person's height, a readout switch is depressed to activate the height measurement voice readout means.

In accordance with a further aspect of a preferred form of the invention, the electronic control circuit additionally includes a mode range control switch for setting the electronic control circuit to conform with actual position of the measurement device on a wall. For example, in one mode range, the control circuit is set for providing measurement readout within a range of two feet to four feet, whereas in a second mode range the control circuit is set to provide measurement readout in a range of four feet to six feet.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

Figure 1:
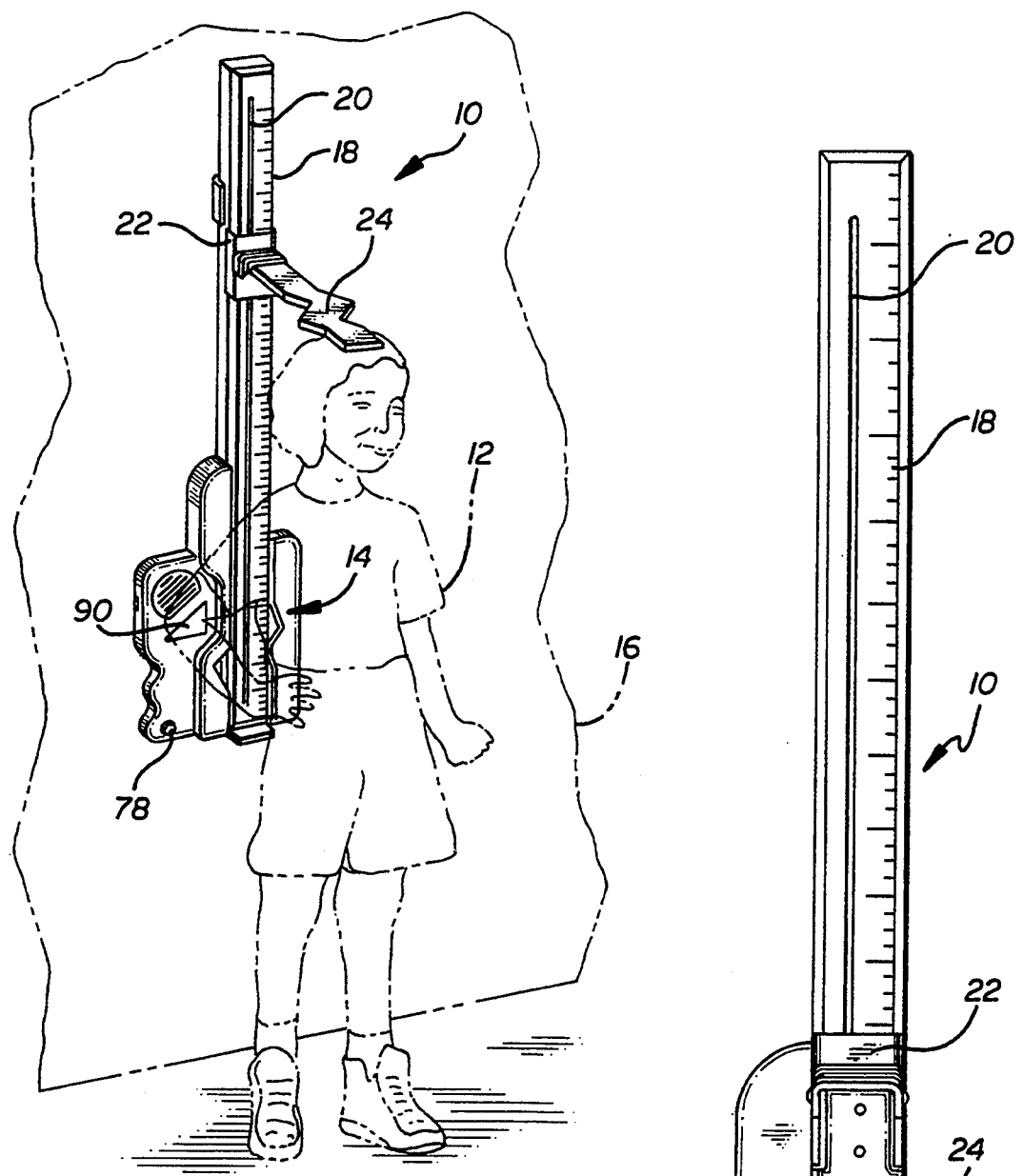
FIG. 1 is a perspective view illustrating the height measurement device embodying the novel features of the invention, and depicting the device mounted on a wall in an operative position for measuring a person's height.

As shown in the exemplary drawings, a height measurement device referred to generally in FIG. 1 by the reference numeral 10 is provided for quickly and easily measuring the height of a person, particularly such as a child 12. The measurement device 10 is designed for operation and manipulation by a single person, without the aid or assistance of a second person. Operation of the measurement device is accompanied by the generation of audio novelty signals and voice commands, with a voice readout of the measured height.

Figure 2:
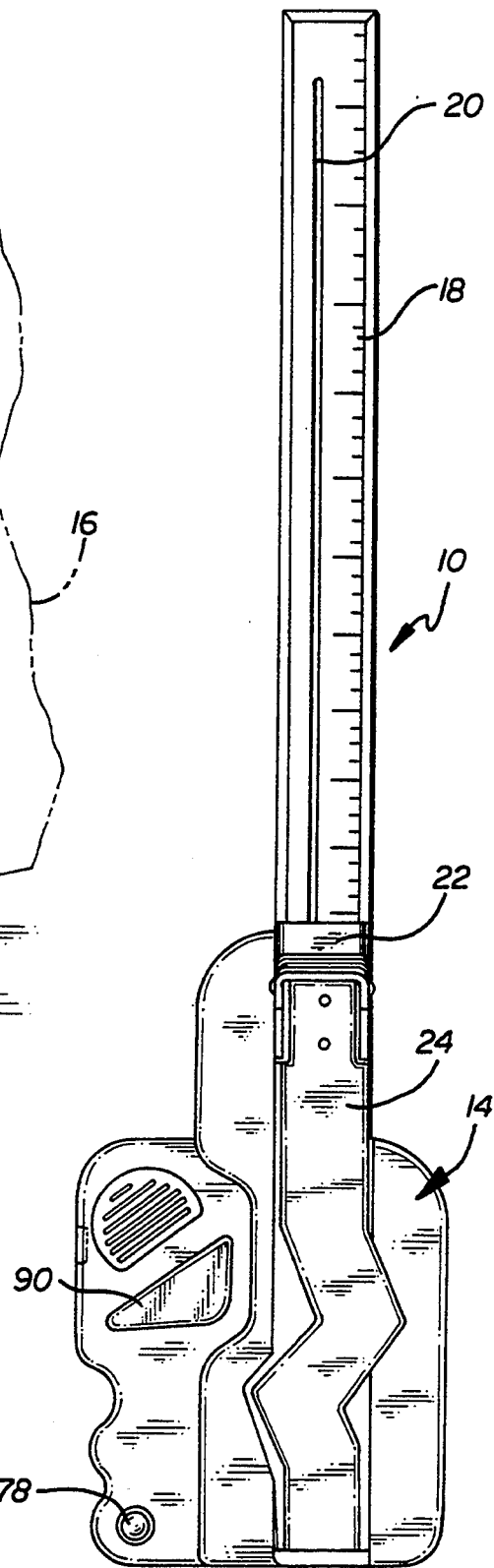
FIG. 2 is a front plan view of the height measurement device.

As shown generally in FIGS. 1 and 2, the measurement device 10 comprises a housing 14 adapted for convenient mounting onto a wall 16, such as a wall in a child's bedroom within a residential dwelling. The illustrative drawings depict the housing to have a novelty shape, shown in the general form a guitar. Importantly, however, the housing includes a vertical scale 18 disposed alongside a vertical slide track 20. A mechanical slide 22 is movable along the length of the track 20 to position a measurement arm 24 at a position representing the height of a person 12. An electronic control circuit 26 (FIG. 5) responds to the vertical position of the mechanical slide 22 to provide a height measurement readout. In accordance with one aspect of the present invention, the height measurement readout is in the form of a synthesized voice readout.

Figure 3:
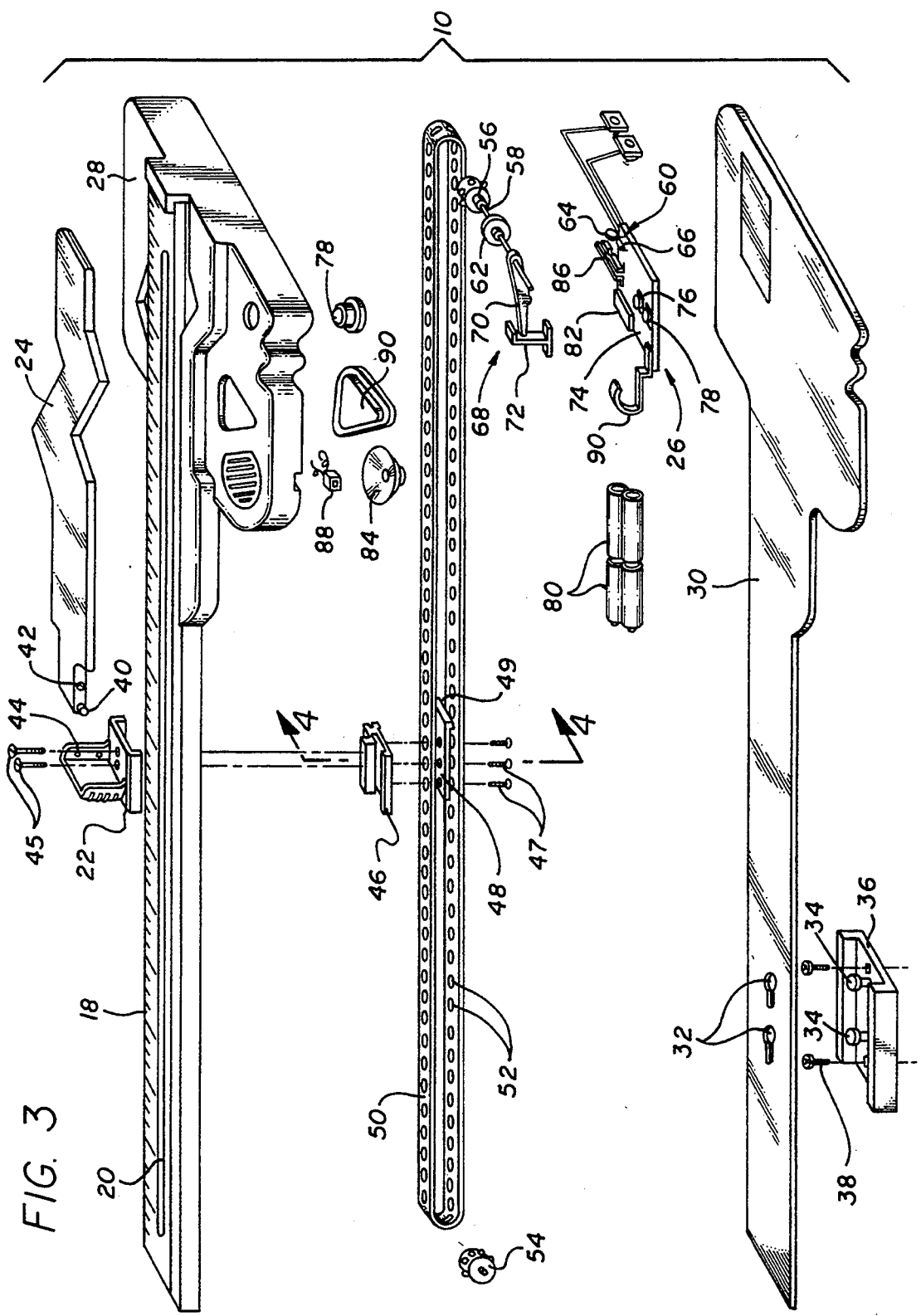
FIG. 3 is an exploded perspective view, shown somewhat in schematic form, illustrating assembly of the components forming the height measurement device.

As shown best in FIG. 3, the device housing 14 includes a front housing member 28 adapted for assembly with a rear housing panel 30 to enclose and support the operating components of the device. The rear panel 30 includes one or more keyhole apertures 32 for receiving mounting pegs 34 protruding from a wall bracket 36. The wall bracket 36 is adapted for mounting onto the selected wall 16 in a conventional manner, such as by use of screws 38, to position the bracket 36 and the measurement device 10 mounted thereon at a selected position relative to the floor. In this regard, as will be described in more detail, the electronic control circuit 26 includes mode range selection means for accommodating mounting of the wall bracket 36 at one of two different vertical positions.

The mechanical slide 22 carries the measuring arm 24 for movement between a stored position resting substantially flush against the front face of the housing 14, and a deployed position extending forwardly and substantially horizontally from the housing. In the illustrative drawings, the measuring arm 24 is shown connected to the slide 22 by pivot pins 40. Detent components 42 and 44 are formed respectively on the measuring arm 24 and the slide 22 for interengagement to releasibly lock the arm 24 in the horizontal position (FIGS. 1 and 4) when a height measurement is to be taken. At other times, the measuring arm 24 can be pivoted downwardly about the pivot pins 40 to lie substantially flat against the device housing 14 (FIG. 2).

The slide 22 is positioned along the vertical track 20, in a position alongside the vertical scale 18. The track 20 is defined by an elongated vertical slot formed in the front housing member 28. The slide 22 is connected by screws 45 or the like to a slide guide 46 disposed at the inboard side of the track slot. The slide guide 46 is secured in turn by additional screws 47 or the like and a belt keeper plate 48 to a measurement belt 50. The belt 50 is formed with a uniformly spaced succession of apertures 52 for positive drive engagement with a pair of sprocket wheels 54 and 56 mounted within the housing 14 respectively at the upper and lower ends of the vertical scale 18. With this construction, vertical displacement of the slide 22 with the measuring arm 24 along the track 20 results in a corresponding displacement of the belt 50 about the sprocket wheels 54, 56.

Figure 5:
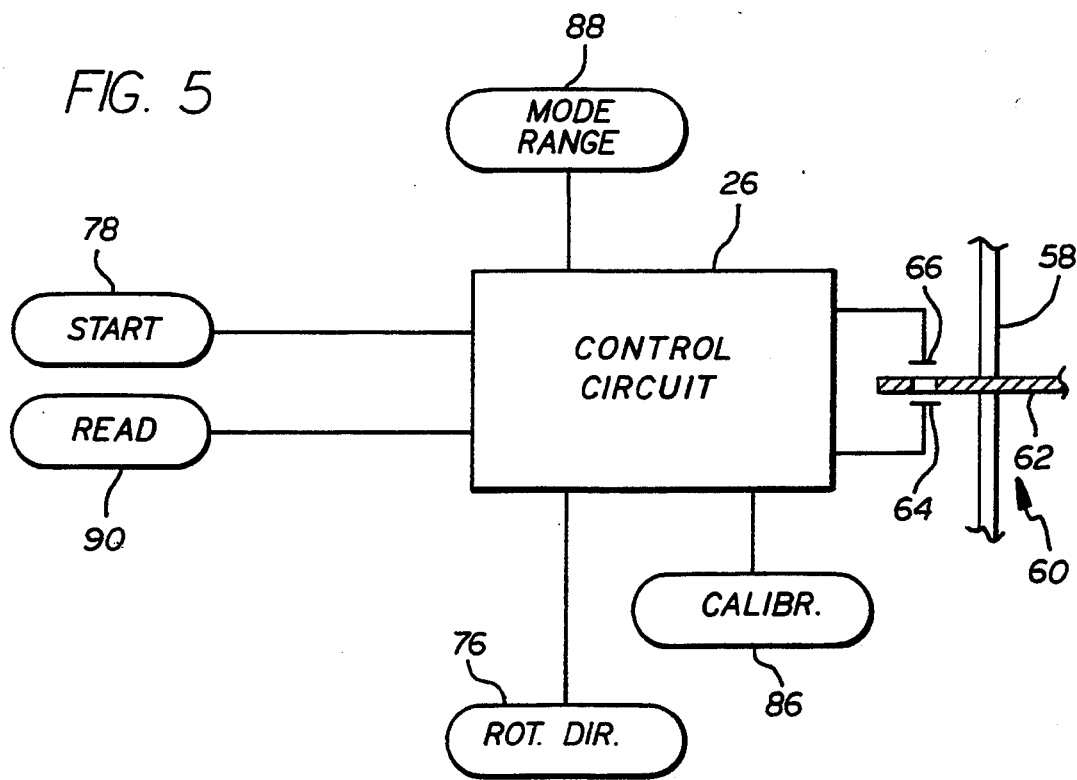
FIG. 5 is a schematic diagram showing an electronic control circuit in block form, in relation to a plurality of input switches.

The lower sprocket wheel 56 is carried on a rotatable drive shaft 58. An optical sensor unit 60 includes an apertured sensor wheel 62 mounted on the drive shaft 58 in a position between a light source 64 and a light detector 66 coupled to the electronic control circuit 26 (FIGS. 3 and 5). Accordingly, the optical sensor unit 60 incrementally signals the control circuit 26 as the slide 22 is displaced vertically along the track 20, as a result of the sensor wheel 62 interrupting the optical link between the source 64 and the detector 66. In the preferred form of the invention, the spacing of the apertures formed near the periphery of the sensor wheel 62 is chosen to interrupt this optical link each time the slide 22 is moved one-fourth inch.

Direction sensor means 68 are provided to detect the direction of vertical displacement of the slide 22, and to correspondingly signal the control circuit 26 so that the monitored slide position can be incremented or decremented, as appropriate. More particularly, as shown in FIG. 3, a direction sensor arm 70 is mounted on the drive shaft 58 in a slip-fit manner for displacement back-and-forth between limit stops defined by a stop bracket 72. In one direction of shaft rotation, the sensor arm 70 is lifted from the underlying circuit board 74 having the control circuit 26 thereon, whereas, in the opposite direction of shaft rotation, the sensor arm 70 is displaced toward the board 74 for contact with a direction sensor switch 76. Depression of this sensor switch 76 is effective to signal the control circuit 26 that the slide 22 is being moved in one direction, namely, upward in the embodiment shown in FIG. 3, whereas, nondepression of the switch 76 is effective to signal the control circuit 26 that the slide 22 is being moved downwardly.

Figure 4:
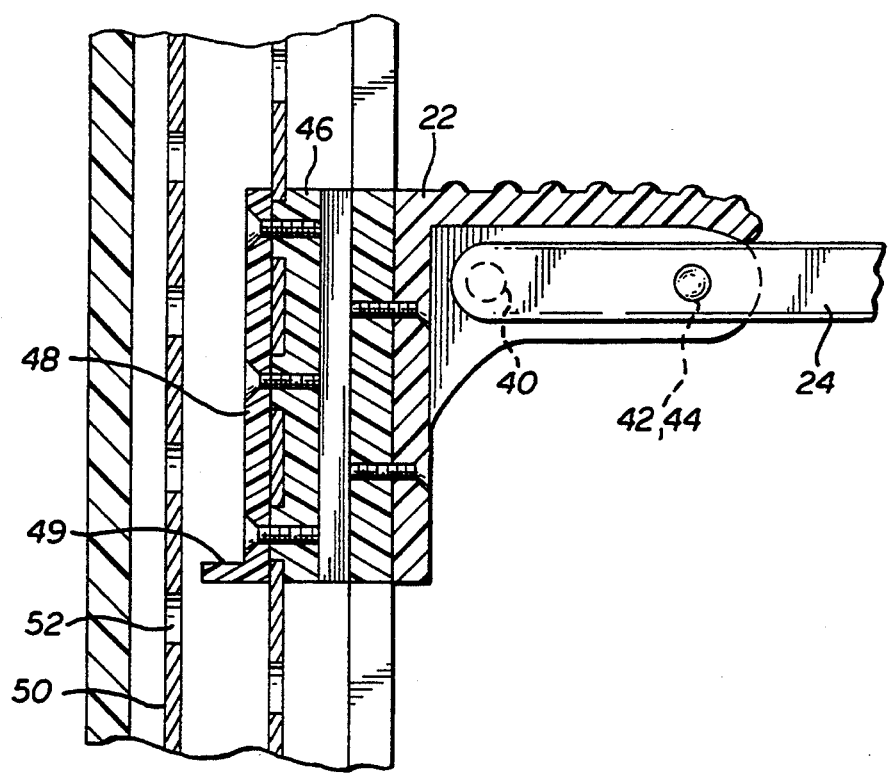
FIG. 4 is an enlarged fragmented sectional view taken generally on the line 4—4 of FIG. 3.

As shown in FIGS. 3 and 4, the control circuit 26 additional includes a start button or switch 78 for initiating operation of the measurement device. Electrical power is conveniently provided by batteries 80, although it will be understood that alternative power sources may be used. An audio chip 82 having voice synthesizer capability is also provided to produce selected audio and voice outputs via a speaker 84.

Figure 6:
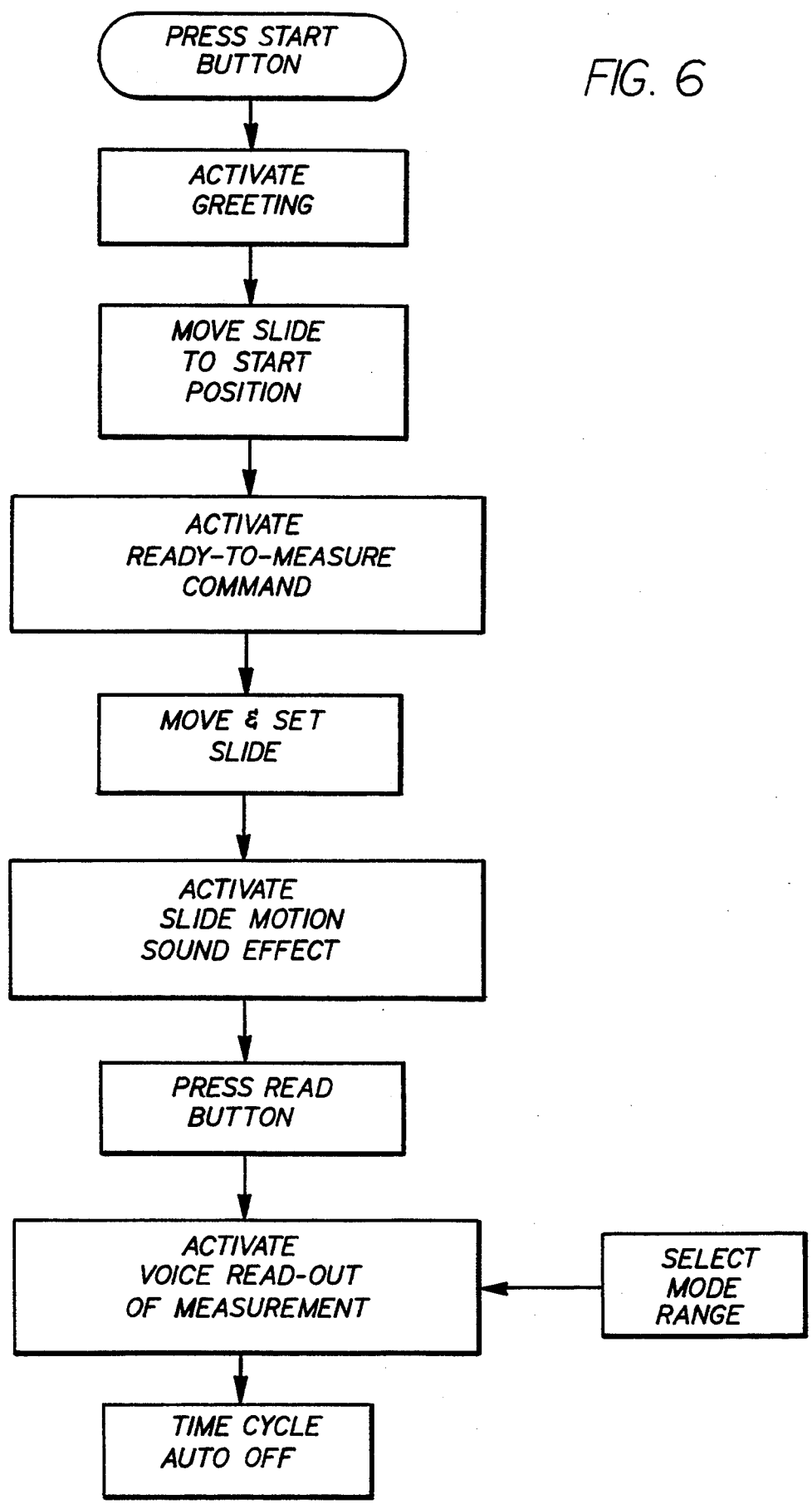
FIG. 6 is a functional flow chart representing the form and operation of the electronic control circuit for use in the invention.

In the preferred form of the invention, and with reference to the flow chart of FIG. 6, depression of the start button 78 activates the control circuit 26 to initiate operation of the measurement device 10. When depression of the start button 78 occurs, the measuring arm 24 carried by the slide 22 is normally in the stored position (FIG. 2) lying flush against the housing 14. As an initial step, the control circuit 26 respond s to depression of the start button 78 to produce a voice command instructing the person operating the device to deploy the measuring arm 24 and to move the slide 22 to the "start" position. This "start" position comprises the lowermost position of the slide 22 along the track 20. This initial voice command is desirably accompanied by a voice greeting such as "hello", and preferably one of a plurality of voice greetings selected at random each time the start button 78 is depressed.

Movement of the slide 22 to the "start" position causes tab 49 on the slide keeper plate 48 to contact a calibration switch 86 connected to the control circuit 26. The calibration switch is thus capable of signalling the control circuit that the slide 22 and measuring arm 24 carried thereby have been placed in a known reference position. In this regard, a mode range selection switch 88 is also provided to set the control circuit 26 for measuring heights within different vertical ranges. For example, in the embodiment shown, the mode range switch 88 can be set to a first position setting the control circuit 26 to provide height readings within the range of two to four feet, or to a second position to provide height readings within the range of four to six feet. Thus, in this example, the measuring arm 24 is positioned at either two feet or at four feet above the floor when the slide 22 is moved to the "start" position, depending upon the setting of the mode range control switch 88. The position of the mode range switch 88 is, of course, chosen in accordance with the vertical mounting position of the measurement device 10 on the wall 16.

When the slide 22 is placed in the "start" position, as described, the control circuit 26 activates the audio chip 82 to command the operator to move the measuring arm 24 to the desired position representing the person's height. Initially, such movement entails upward displacement of the slide 22 along the track 20, although alternating upward and downward movements will often be performed before the measuring arm 24 is placed in the desired position seated firmly on top of the person's head as shown in FIG. 1. The actual vertical position of the slide 22 and arm 24 are tracked by the control circuit 26, by virtue of the input from the optical sensor unit 60 and the directional sensor switch 70. In addition, the vertical up and down displacement of the slide 22 is desirably accompanied by novelty audio output from the audio chip 82, such as a novelty signal of increasing pitch as the slide is raised, and vice versa.

When the desired height measurement position of the arm 24 is reached, the person 12 depresses a readout button or switch 90. This signals the control circuit 26 to generate a synthesized voice output constituting a voice readout of the measured height. As noted previously herein, the control circuit 26 has monitored the vertical position of the slide 22 in one-fourth inch increments, and thus can provide the voice readout with an accuracy to one-fourth inch. The voice readout is desirably accompanied with an additional greeting or salutation, such as "congratulations, you have grown". Once again, in the preferred form of the invention, such additional greeting or salutation may be randomly selected from a group of such messages. At the conclusion of the voice readout, the control circuit 26 is designed to switch to a power-off state within a selected period of a few minutes.

The height measurement device of the present invention is particularly designed to be operated by one person such as a child without the assistance of an adult or any other person to provide accurate height measurements in association with novelty synthesized voice commands and readouts and/or other audio signals.

A variety of modifications and improvements to the invention shown and described herein will be apparent to those skilled in the art. Accordingly, no limitation on the invention is intended by way of the foregoing description and accompanying drawings, except as set forth in the appended claims.

What is claimed is:

1. A height measurement device comprising:
   a housing adapted for mounting onto a wall;
   a measuring arm carried by said housing for vertical displacement manually within a selected height measurement range to a position seated on top of a person's head to represent that person's height;
   a control circuit including voice synthesizer means for producing preprogrammed voice audio outputs, said control circuit further including audio means for producing an audio signal in response to said vertical displacement of said measuring arm;
   start means on said housing for activating said control circuit to generate instructional voice commands to explain how to operate said device;
   said control circuit including means for tracking the vertical position of said measuring arm and for correlating said vertical position with a height measurement; and
   readout means for activating said control circuit to generate a voice readout announcing the vertical position of said measuring arm.

2. The height measurement device of claim 1 further including mode range control means for variably selecting said height measurement range in accordance with the vertical position of said housing on the wall.

3. The height measurement device of claim 1 further including a calibration switch connected to said control circuit, said instructional commands including commands to displace said measuring arm to a reference position for contacting said calibration switch and thereby signalling said control circuit that said measuring arm is in said reference position.

4. The height measurement device of claim 3 wherein said instructional commands further include commands to move said measuring arm from said reference position to said position seated on top of the person's head representing that person's height.

5. The height measurement device of claim 1 wherein said audio signal comprises a signal of increasing pitch in response to upward movement of said measuring arm, and a signal of decreasing pitch in response to downward movement of said measuring arm.

6. The height measurement device of claim 1 wherein said means for tracking the vertical position of said measuring arm comprises an optical sensor unit.

7. The height measurement device of claim 6 wherein said optical sensor unit includes means for monitoring the direction of movement of said measuring arm.

8. The height measurement device of claim 1 wherein said housing defines a vertical track, and said height measurement device further including a slide, and belt means carried by said housing for mounting said slide for vertical displacement along said track, said measuring arm being carried by said slide.

9. The height measurement device of claim 8 further including means for pivotally mounting said measuring arm to said slide for movement between a deployed position projecting outwardly from said housing and a stored position lying against said housing.

10. The height measurement device of claim 1 wherein said start means comprises a manually operated start button on said housing.

11. The height measurement device of claim 10 wherein said readout means includes a manually operated readout button on said housing.

12. The height measurement device of claim 1 wherein said readout means includes a manually operated readout button on said housing.

13. A height measurement device comprising:
   a housing adapted for mounting onto a wall;
   a measuring arm carried by said housing for vertical displacement within a selected height measurement range to a position seated on top of a person's head to represent that person's height; and
   a control circuit including audio means for producing an audio signal in response to said vertical displacement of said measuring arm, said control circuit further including means for tracking the vertical position of said measuring arm and for correlating said vertical position with a height measurement, and said device further including readout means for activating said control circuit to indicate the height measurement.

14. The height measurement device of claim 13 wherein said control circuit further includes voice synthesizer means for producing preprogrammed voice audio outputs, said readout means activating said control circuit to generate a voice readout announcing the vertical position of said measuring arm.

15. The height measurement device of claim 13 wherein said device further includes start means on said housing for activating said control circuit to generate instructional voice commands to explain how to operate said device.

16. The height measurement device of claim 13 wherein said audio signal comprises a signal of increasing pitch in response to upward movement of said measuring arm, and a signal of decreasing pitch in response to downward movement of said measuring arm.

* * * * *